(12) United States Patent
Chen et al.

(10) Patent No.: US 10,509,979 B2
(45) Date of Patent: *Dec. 17, 2019

(54) INSPECTION METHODS AND SYSTEMS

(71) Applicant: NUCTECH COMPANY LIMITED, Beijing (CN)

(72) Inventors: Zhiqiang Chen, Beijing (CN); Li Zhang, Beijing (CN); Ziran Zhao, Beijing (CN); Yaohong Liu, Beijing (CN); Duokun Zhang, Beijing (CN); Jianping Gu, Beijing (CN); Qiang Li, Beijing (CN); Jian Zhang, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/255,738

(22) Filed: Jan. 23, 2019

(65) Prior Publication Data

US 2019/0156139 A1     May 23, 2019

Related U.S. Application Data

(63) Continuation of application No. 15/129,389, filed as application No. PCT/CN2015/098476 on Dec. 23, 2015, now Pat. No. 10,229,336.

(30) Foreign Application Priority Data

Dec. 30, 2014   (CN) .......................... 2014 1 0844405

(51) Int. Cl.
| | | |
|---|---|---|
| *G06K 9/32* | (2006.01) | |
| *G01V 5/00* | (2006.01) | |
| *G01N 23/046* | (2018.01) | |

(52) U.S. Cl.
CPC ......... *G06K 9/3241* (2013.01); *G01N 23/046* (2013.01); *G01V 5/0016* (2013.01); *G01V 5/005* (2013.01)

(58) Field of Classification Search
CPC ...... G06K 9/3241; G01N 23/04; G01N 23/10; G01N 2223/618; G01N 2223/637;
(Continued)

(56) References Cited

U.S. PATENT DOCUMENTS

| | | | |
|---|---|---|---|
| 6,111,974 A | 8/2000 | Hiraoglu et al. | |
| 10,229,336 B2 * | 3/2019 | Chen .................... | G01V 5/0016 |

(Continued)

FOREIGN PATENT DOCUMENTS

| | | |
|---|---|---|
| CN | 1802676 A | 7/2006 |
| CN | 101558327 A | 10/2009 |

(Continued)

OTHER PUBLICATIONS

International Patent Application No. PCT/CN2015/098476; Search Report; dated Mar. 18, 2016; 2 pages.
(Continued)

*Primary Examiner* — Courtney D Thomas
(74) *Attorney, Agent, or Firm* — BakerHostetler

(57) ABSTRACT

An inspection method and system for inspecting whether there is any liquor in goods is provided. The method includes: acquiring a radiation image of goods being inspected; processing on the radiation image to obtain an ROI; inspecting on the ROI using a liquor goods inspection model to determine if the ROI of the radiation image contains liquor goods. The above solution performs liquor inspection on scanned images of goods, especially containers, so as to intelligently assist the image inspectors.

10 Claims, 3 Drawing Sheets

(58) Field of Classification Search
CPC ........... G01N 2223/639; G01N 23/046; G01V 5/0016; G01V 5/0008
See application file for complete search history.

(56) References Cited

U.S. PATENT DOCUMENTS

| | | |
|---|---|---|
| 2004/0252024 A1 | 12/2004 | Huey et al. |
| 2005/0058242 A1 | 3/2005 | Peschmann |
| 2005/0117700 A1 | 6/2005 | Peschmann |
| 2007/0280416 A1* | 12/2007 | Bendahan .............. G01N 23/04 378/57 |
| 2009/0290757 A1 | 11/2009 | Mian et al. |

FOREIGN PATENT DOCUMENTS

| | | |
|---|---|---|
| CN | 101606084 A | 12/2009 |
| CN | 102483965 A | 5/2012 |
| CN | 103679195 A | 3/2014 |
| CN | 104237262 A | 12/2014 |
| GB | 2441551 A | 3/2008 |
| WO | WO 2008/034232 A1 | 3/2008 |

OTHER PUBLICATIONS

European Patent Application No. 15202838.7; Extended Search Report; dated May 13, 2016; 8 pages.
Zhang et al.; "Joint Shape and Texture Based X-Ray Cargo Image Classification"; IEEE Conf. on Computer Vision and Pattern Recognition Workshops; 2014; p. 266-273.
Singapore Patent Application No. 11201607836W; Written Opinion; dated Mar. 10, 2017; 5 pages.

\* cited by examiner

INSPECTION METHODS AND SYSTEMS

CROSS REFERENCE TO RELATED APPLICATION

This application is a continuation of U.S. application Ser. No. 15/129,389 filed Sep. 26, 2016, which is the national stage of International Application No. PCT/CN2015/098476 filed Dec. 23, 2015, which claims the benefit of Chinese Patent Application No. 201410844405.3, filed Dec. 30, 2014, the entire contents of which are incorporated herein by this reference.

TECHNICAL FIELD

The disclosure relates to automatic inspection of suspect objects based on radiation images, and particularly to automatic inspection methods and systems for liquor goods in a large container scanning system.

BACKGROUND

Security inspection plays an essential role in fields of anti-terrorism, drug trading, smuggling and the like. Governments all over the world are paying more attention on combating smuggling, and inspection standards for custom containers, luggage, and other sensitive goods have been raised to a higher level. Recently, liquor smuggling appears to have perceptible impact on domestic liquor market. It not only disturbs regular economic order and causes tremendous tax loss of the nation, but also may provide funds for terrorist attacks and other criminal activities. Thus, striking liquor smuggling is of significant meaning.

Large-amount liquor smuggling is typically carried out via containers, thus ordinary inspection approaches are not capable of correctly detecting all types of liquors. Moreover, such inspection approaches normally requires opening the containers, which is not always feasible in practice. X-ray imaging preforms radiography on goods, luggage and the like, so as to conduct inspection without opening the package. X-ray imaging technology is already widely applied in airports, customs, and train stations, and currently serves as an important approach for illegal object inspection. However, in the process of image inspection, an image inspector is required to determine what is enclosed in the container being inspected, and erroneous judgments are inevitable since the number of categories of goods may be too large for a person to clearly distinguish. Furthermore, different image inspectors may vary a lot in practical experiences. Additionally, human inspection effect may reduce a lot when fatigue arises to the inspector after long time working. Therefore, intelligent inspection functionality in an automatic way is urgently demanded to assist human inspection.

SUMMARY

In order to address the above issues in the prior art, the present disclosure provides inspection methods and systems that are capable of determining if goods are liquor goods.

According to one aspect of the disclosure, an inspection method is provided. The inspection method includes: acquiring a radiation image of goods being inspected; processing on the radiation image to obtain an ROI (region of interest); inspecting on the ROI using a liquor goods inspection model to determine if the ROI of the radiation image contains liquor goods.

Preferably, the step of inspecting on the ROI using a liquor goods inspection model including: extracting shape information and texture information of a local target from the ROI; classifying the shape information and the texture information of the local target from the ROI using the liquor goods inspection model established based on shape features and texture features of the local target, so as to determine if the ROI of the radiation image contains liquor goods.

Preferably, the ROI is inspected in multiple-scales using the liquor goods inspection model.

Preferably, the step of processing on the radiation image including: detecting air regions and impenetrable regions in the radiation image; excluding the air regions and the impenetrable regions from the ROIs.

Preferably, the inspection method further includes a step of: training the liquor goods inspection model by way of manually labeling using scanned images of known goods categories where liquor goods are contained and scanned images of goods that is similar to liquors but not liquors.

Preferably, the manually labeling includes: labeling positions and placing postures of the liquor goods in the image.

Preferably, the liquor goods inspection model is established through a weighted summation of shape features and texture features of the local targets in samples, wherein weights in the weighted summation is related to regional conditional entropy.

Preferably, the inspection method further includes a step of: for those liquor goods that are not detected using the liquor goods inspection model and those goods that are detected using the liquor goods inspection model as liquor goods but turns out to be non-liquor goods, re-training the liquor goods inspection model by manually labeling.

Preferably, the liquor goods inspection model is established with respect to different placing postures of liquor goods.

According to another aspect of the disclosure, an inspection system is provided. The inspection system includes: a scanning imaging system configured to scan goods being inspected so as to acquire a radiation image of the goods being inspected; a data processing apparatus configured to process on the radiation image to obtain an ROI, and to inspect on the ROI using a liquor goods inspection model to determine if the ROI of the radiation image contains liquor goods.

Preferably, the data processing apparatus is configured to extract shape information and texture information of a local target from the ROI, and to classify the shape information and the texture information of the local target from the ROI using the liquor goods inspection model established based on shape features and texture features of the local target so as to determine if the ROI of the radiation image contains liquor goods.

With the solution as stated above, it is possible to conduct automatically liquor inspection, such that inspection accuracy and efficiency can be improved effectively.

BRIEF DESCRIPTION OF THE DRAWINGS

To better illustrate the disclosure, embodiments of the disclosure will be described below with respect to the following drawings, wherein.

In the drawings, not all circuits or structures in the embodiments are shown. Throughout the drawings, like reference numbers indicate like or similar parts or features.

THE DESCRIPTION OF EMBODIMENTS

The specific embodiments of the present disclosure will be described in detail below. It should be noted that the embodiments herein are used for illustration only, without limiting the present disclosure. In the description below, a number of specific details are explained to provide better understanding of the present disclosure. However, it is apparent to those skilled in the art that the present disclosure can be implemented without these specific details. In other instances, well known circuits, materials or methods are not described specifically so as not to obscure the present disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurred in various positions throughout the specification may not necessarily refer to the same embodiment or example. Furthermore, specific features, structures or properties may be combined into one or more embodiments or examples in any appropriate combination and/or sub-combination. Moreover, it should be understood by those skilled in the art that the term "and/or" used herein means any and all combinations of one or more listed items.

In order to address the above issues in prior art, the embodiments in the disclosure propose to acquire a radiation image of the goods being inspected using a radiation imaging device, and then process on the radiation image to obtain an ROI. The ROI is inspected using a liquor goods inspection model to determine if the ROI of the radiation image contains liquor goods. Hence, it is enabled to automatically inspect if there is any liquor goods in the radiation image obtained by scanning the container with X-ray without opening the container. If there is any liquor, then its position is indicated in the radiation image so as to assist in security inspection. In embodiments of the disclosure, liquor goods inspection mainly relies on detection of liquor bottles, such as bottles of specific types.

Additionally, the inspection system in embodiments of the disclosure possesses functionality for online learning. For example, the system can conduct online learning on typical images that are surely liquor but cannot be detected and those that are detected as liquor but are actually not, and automatically updates its inspection algorithm to eliminate impacts of the variation of bottles or postures on the inspection result.

Figure 1A:
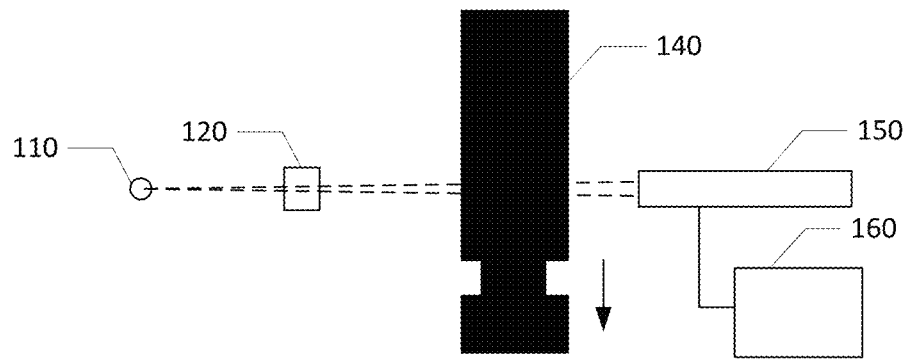
FIGS. 1A and 1B are structural diagrams for an inspection system in accordance with one embodiment of the disclosure.
Figure 1B:
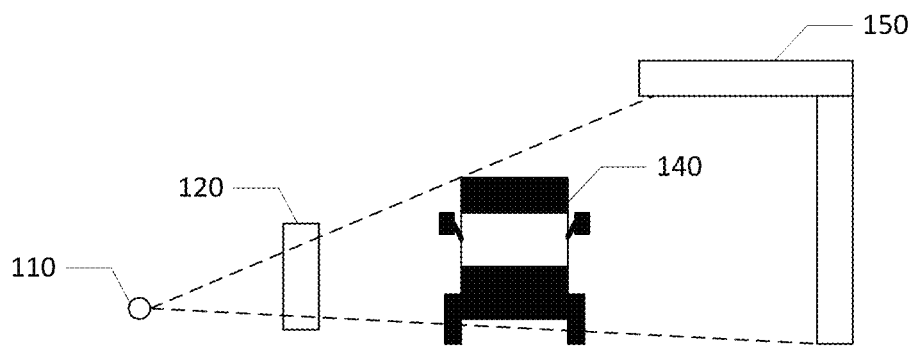

FIGS. 1A and 1B are structural diagrams for an inspection system in accordance with one embodiment of the disclosure. FIG. 1A shows a top view of the inspection system, and FIG. 1B shows a front view of the inspection system. As shown in FIGS. 1A and 1B, X-ray source 110 generates X-ray, and the generated X-ray is transmitted to a moving container truck 140 to conduct security inspection after aligned by an aligner 120. The X-ray penetrates the truck 140, and the penetrated X-ray is received by a detector 150, and then transformed into digital signals and stored in a data processing apparatus 160 such as a computer to obtain a radiation image. According to embodiments of the disclosure, after the radiation image of the container truck 140 is obtained by scanning, the image is processed at the data processing apparatus 160 to obtain an ROI, such as main goods region. Then, the ROI is inspected using a liquor goods inspection model to determine if the ROI of the radiation image contains liquor goods.

Figure 2:
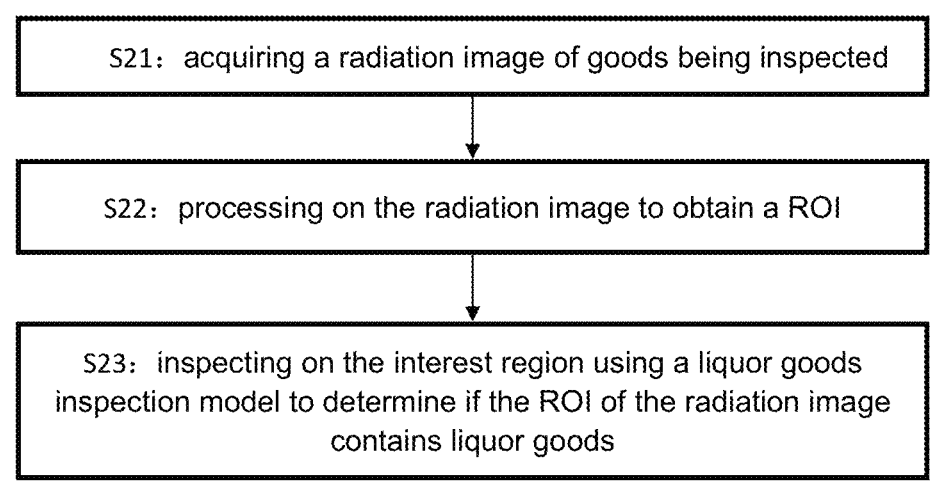
FIG. 2 is a flow chart for an inspection method in accordance with embodiments of the disclosure.

FIG. 2 is a flow chart for an inspection method in accordance with embodiments of the disclosure. As shown in FIG. 2, at Step S21, a radiation image of the goods being inspected is acquired via an X-ray scanning system. For example, when a container truck passes through the inspection zone at a certain speed, a radiation image will be produced. The acquired image may vary slightly due to differences with respect to parameters such as energy/dose of X-ray source, size of detector, mechanical structure, vehicle speed and beam frequency. In some embodiments, based on requirements, normalization process should be performed on the radiation image first, the normalization process may include brightness normalization and resolution normalization (where the resolution is collectively scaled to 5×5 mm/pixel).

At Step S22, the radiation image is processed to obtain an ROI. In some embodiments, based on requirements, preprocessing may be performed on the radiation image. The preprocessing is intended to remove impact of air regions and impenetrable regions in the image. In the disclosure, the air regions and impenetrable regions are detected by directly setting a threshold. Such regions are removed to obtain an ROI. Avoiding impact of the air regions and impenetrable regions when inspecting liquor goods may expedite the inspection process and reduce occurrences of false alarms. In other embodiments, regions other than the main goods region may be excluded, that is, the main goods region is taken as the ROI.

At Step S23, the ROI is inspected using a liquor goods inspection model to determine if the ROI of the radiation image contains liquor goods. For example, the ROI may be inspected using a liquor goods inspection model that is previously trained with sample images. During establishment of the model, similar preprocessing may be conducted on the sample images. Then, features are extracted, and the liquor goods inspection model is established on the basis of the extracted features. Then, the model may be trained with pre-generated sample library (for example, including positive sample library and negative sample library). Moreover, online learning and training and re-training may be conducted in the inspection process.

Particularly, shape information and texture information of a local target from the ROI may be extracted. Then, the shape information and the texture information of the local target from the ROI may be classified using the liquor goods inspection model established based on shape features and texture features of the local target, so as to determine if the ROI of the X-ray image contains liquor goods. Processes for feature extraction, model establishment and model updating will be described in detail as below.

Image feature extraction is the first step of object classifying and inspecting. Low-level feature extraction generally includes: interest point detection based extraction and dense based extraction. The interest point detection may be for example Harris corner points detection, Features from Accelerated Segment Test (FAST) operation, Laplacian of Gaussian (LoG) Difference of Gaussian (DoG), etc. Another generally used technique so called dense sampling employed by many local feature descriptors, such as Scale-invariant feature transform (SIFT), Histogram of Oriented Gradient (HOG), Local Binary Pattern (LBP), etc. The contents in X-ray images may vary a lot from each other, thus it may not be sufficient to fulfill practical requirements if only one feature representation is used. For example, HOG feature describes local image gradient or directional density distribution on edge, which may be considered as description of local target representation and shape. On the other side, LBP may be considered as a type of texture information. In target detection application, shape information is more useful than texture information, and both of which are complementary. In the X-ray image, when large goods are individually placed, the texture information is not as evident as shape information. When the goods are compactly stacked up, the shape information is no longer as clear, but the texture feature becomes distinctive. In order to accommodate for various types of goods, in the embodiments of the disclosure, low level features utilize Boosted HOG-LBP to illustrate the X-ray image, for the feature at (i, j):

$$F_{i,j} = \alpha_{i,j} HOG_{i,j} + (-\alpha_{i,j}) LBP_{i,j}$$

where $\alpha_{i,j}$ is a parameter related to regional conditional entropy. $HOG_{i,j}$ and $LBP_{i,j}$ respectively indicate HOG feature and LBP feature at the position. The regional conditional entropy is relatively small at regions with smaller goods densities, so that the texture feature will account for larger proportion.

Additionally, in order to improve detection performance, in embodiments of the disclosure, mid-level features (i.e. local outstanding image tiles) may be used to illustrate the most original information. Such mid-level features may be clustered from massive image tiles.

Training of a classifying model (also referred to as detection model, since classifying means detecting when there are two categories) requires a lot of labeled positive samples (there is no need to tag negative samples). Currently, positive samples are usually manually labeled. Weak labeling can reduce participation of human, and thus make the labeling process simple and efficient. The embodiments use two methods to perform labeling: 1) identifying approximate positions of liquor goods in the image with a rectangle, and a variable is used to describe placing postures of liquors, where the positions and postures are used as hidden variables during model training; 2) weak labeling are realized by two steps of "positioning plus detecting".

Figure 3:
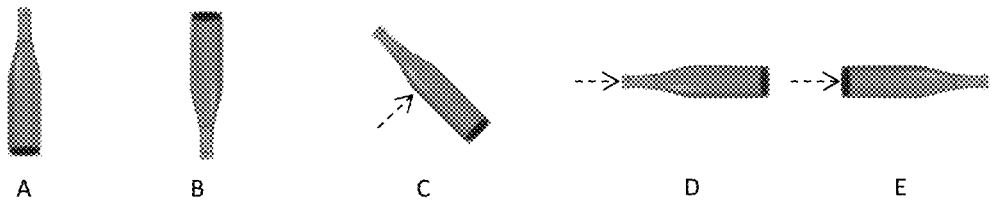
FIG. 3 shows a placing posture of liquor (the dashed arrows indicate directions of the X-rays)

The "positioning plus detecting" method belongs to weak labeling algorithm, that is, if a sample X-ray image is presented, it is only necessary to tell if there is any liquor and how is liquor bottle placed. In practice, the bottles are generally erectly piled in the container. Though the bottles may be also laid down or piled in an upside-down manner, such instances are rare. As shown in FIG. 3, there are generally five kinds of placing postures of liquor bottles: A. erect; B. upside-down; C. laid down with the axis of the bottle perpendicular to the X-ray; D. laid down with the axis of the bottle reversely parallel to the X-ray; E. laid down with the axis of the bottle parallel to the X-ray. In a radiation image where placing postures of liquor bottles are already known, the bottles are usually regularly stacked, and irregular stacking is rare in massive transportation. Then, the image may be densely divided into image patches with equal sizes, and they are further clustered with clustering algorithm. K-means by simple distance measure may cluster image tiles that are not visually similar into one cluster, therefore, in order to solve this issue, the present application uses detection-type clustering: first, perform clustering using K-means, then, for each cluster, train a classifier with linear SVM, respectively detect for them in the image, the cluster that got the most result is a positive sample, and the region where it is detected is the region that has liquor. After the "positioning plus detecting" process, the position of the liquor in the radiation image may be obtained, then it can operate like the first labeling manner when taking into account the placing posture of the liquor. In the disclosure, either of the two methods may be adopted to handle positive sample labeling.

In the above, approximate region and posture of liquor may be obtained by weak labeling, and with such information, training of inspection model may be carried out. For liquors with similar bottle packages, five component determining equations may be respectively used to inspect liquors with each of the five placing postures. Then, a Multi-Component inspection model may be obtained by combining the five components.

When training the model, the score for each sample x may be:

$$f_\beta = \max_{z \in Z(x), i \in \varphi} \beta_i \cdot \emptyset(x, z)$$

where β is Multi-Component model parameter, $\beta_i$ is the $i_{th}$ component, z and i are both hidden variables, $\emptyset(x, z)$ is feature vector. In the radiation image, sizes of the objects do not change a lot. In the model training process, number of layers of the feature pyramid may be reduced to only two layers.

Specific training process may include two steps:

step 1: randomly sampling image tiles with a certain size in regions that have liquors, as positive samples, randomly sampling a certain amount of image tiles in regions that do not have liquors, as negative samples, and training using SVM to obtain a classifier;

step 2: detecting image tiles containing liquors from images with liquors using the classifier obtained in step 1, as newly aligned positive samples, detecting image tiles from images without liquors using the classifier obtained in step 1, as hard negative samples, and further taking into consideration above negative sample retraining to obtain the inspection model.

The above process is an off-line training (learning) process, in which training data is prepared in advance and the inspection model is obtained by stepwise training. The inspection model obtained via off-line learning with massive training data may meet the requirement of liquor inspection. But in practice, there may be different kinds of liquors and bottles that are not included in the training database and thus cannot be learned in off-line learning. Inspection result for such bottles may be not as good. In this case, human interactive is needed. Typical bottle images that are not detected may be weak labeled by human and may need to be retrained, which is called incremental learning or on-line learning.

Figure 4:
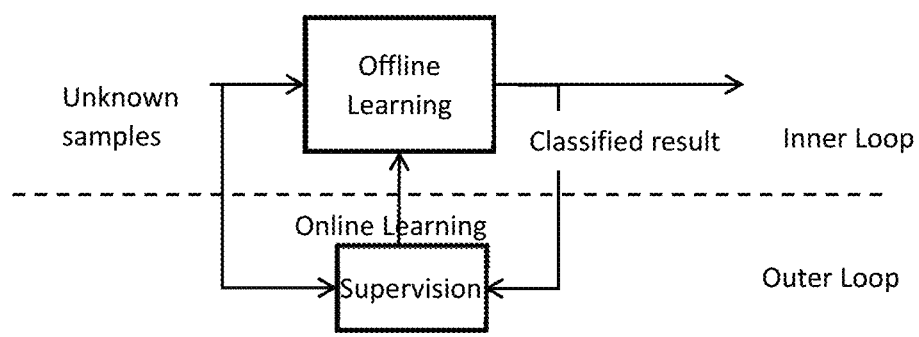
FIG. 4 shows a diagram of conducting an online learning a liquor model in a method in accordance with embodiments of the disclosure.

Actually, offline learning and online learning can be explained by a learning mode combining "inner loop" and "outer loop", as shown in FIG. 4. The inner loop means, for every sample to be inspected, the system uses a model that is well trained offline to process unknown samples. This process does not include human participation. In contrast, outer loop means an image inspector participates in the inspection system in a proper manner, such that a supervised online learning is performed on the liquor goods inspection model and the inspection model is updated, that is, human participate in the inspection process. This manner can be used in an inspection case for special occasions. During online learning, the liquor goods inspection model may be directly updated in a form of Online-SVM, or Online-SVM may be used as a component of the original model. The latter case may train using SVM with one positive sample and a plurality of negative samples.

Figure 5:
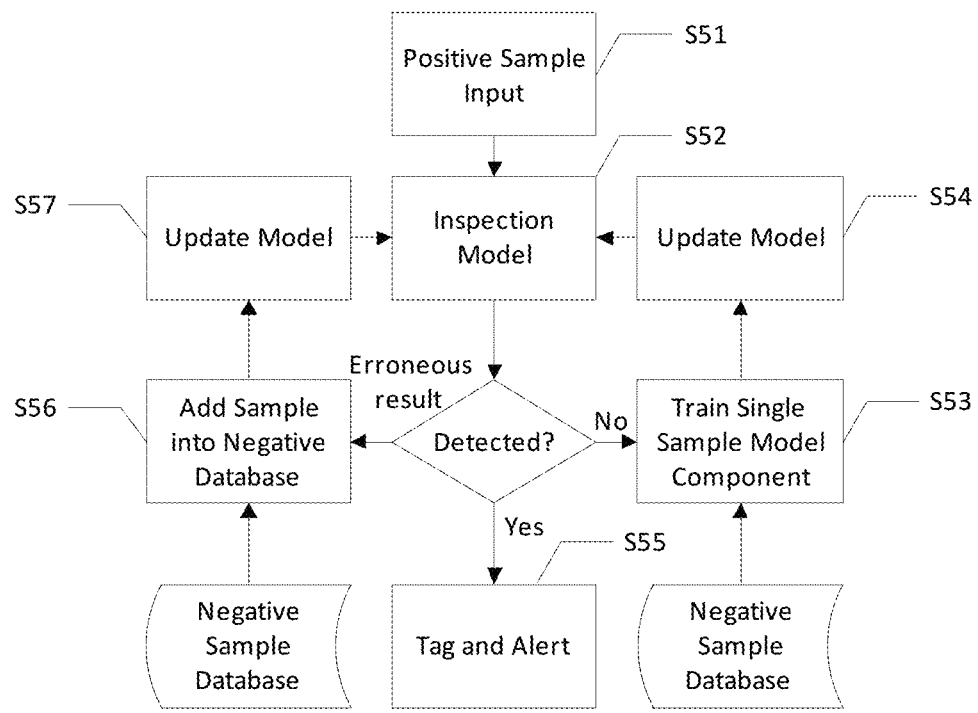
FIG. 5 shows a flow chart of an online learning feedback process based on positive samples in a method in accordance with embodiments of the disclosure.
Figure 6:
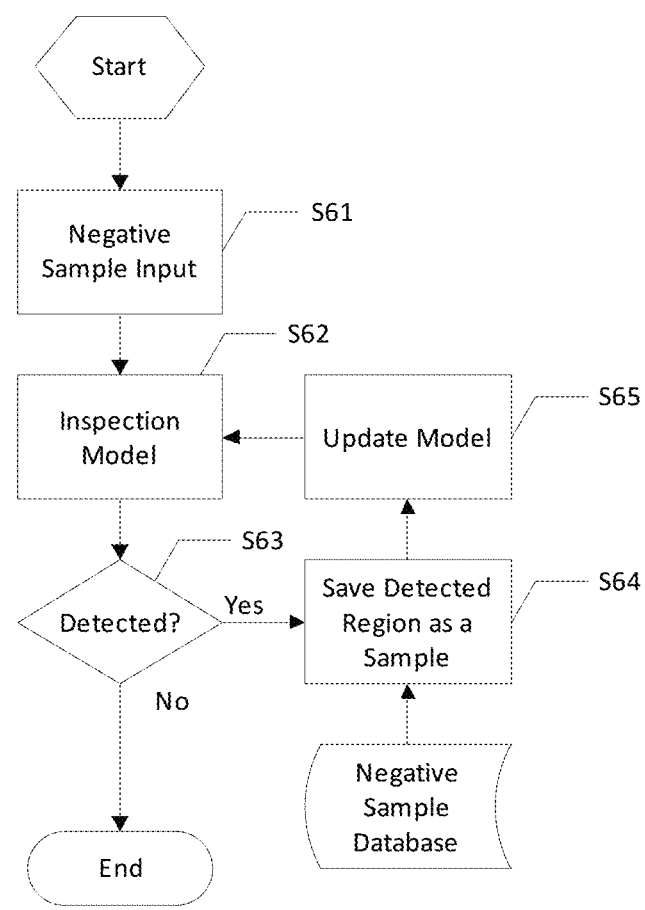
FIG. 6 shows a flow chart of an online learning feedback process based on negative samples in a method in accordance with embodiments of the disclosure.

As to specific operations for the outer loop: the image inspector compares the inspection result and the input sample, and if the result is correct, no supervision operation will be performed; if the result is not correct, the result need to be fed back to the system. FIGS. 5 and 6 show particular feedback mechanisms. As shown in FIG. 5, at Step S51, a radiation image containing liquor is input into the system, and at Step 52 the detection process is performed using inspection model. At Step 53, if no result is showed up and the bottle of liquor is typical, then a component may be trained with one positive sample and a plurality of negative samples, and at Step 54 the model is updated so as to be added into the original model to improve recall rate. If a positive result is detected at Step 55 the goods are labeled and an alert issues. If erroneous result is showed, in conjunction with the characteristics that training model using SVM has high precision and low recall rate, at Step 56 the detected region may be added into negative sample database, to narrow model boundary and reduce erroneous judgments, and then at Step 57 the model is updated. As shown in FIG. 6, at Step 61 a radiation image without liquor is input into the system, and at step S62 a detecting processed is performed using inspection model. If a result is detected at Step 63, then the regional image tile is added into the negative sample database at Step 64, then at Step 65 the model is updated.

Figure 7:
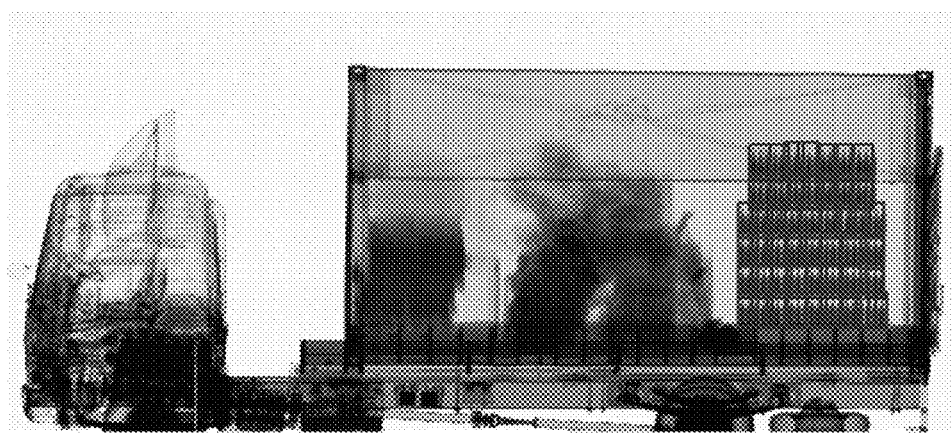
FIG. 7 is a diagram that shows liquor inspection result obtained in an inspection system in accordance with embodiments of the disclosure.

During the inspection of the goods, a sliding window approach is adopted, that is, in an ergodic manner, in which a window with fixed size slides in various scales of the image, and every pixel is computed in every scale to determine if it is a target object. Such a method is conducted in multiple scales, and thus has a higher temporal cost. For an X-ray image, objects in the image are only subject to ignorable significant scale variations. Therefore, in some embodiments, the window may only slide in two image scales, to speed up the inspection while maintaining precision. FIG. 7 is a diagram that shows a liquor inspection result obtained in an inspection system in accordance with embodiments of the disclosure. As shown in FIG. 7, the solution of the present embodiment can identify not only the result but also the placing posture of the liquor bottle.

The solution of the above embodiment performs liquor inspection on scanned images of goods, especially containers, so as to intelligently assist the image inspectors.

The foregoing detailed description has set forth various embodiments of the reconstruction method and spiral CT system via the use of diagrams, flowcharts, and/or examples.

In a case that such diagrams, flowcharts, and/or examples contain one or more functions and/or operations, it will be understood by those skilled in the art that each function and/or operation within such diagrams, flowcharts or examples may be implemented, individually and/or collectively, by a wide range of structures, hardware, software, firmware, or virtually any combination thereof. In one embodiment, several portions of the subject matter described in the embodiments of the present disclosure may be implemented via Application Specific Integrated Circuits (ASICs), Field Programmable Gate Arrays (FPGAs), Digital Signal Processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of those skilled in the art in ray of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present disclosure has been described with reference to several typical embodiments, it is apparent to those skilled in the art that the terms are used for illustration and explanation purpose and not for limitation. The present disclosure may be practiced in various forms without departing from the spirit or essence of the present disclosure. It should be understood that the embodiments are not limited to any of the foregoing details, and shall be interpreted broadly within the spirit and scope as defined by the following claims. Therefore, all of modifications and alternatives falling within the scope of the claims or equivalents thereof are to be encompassed by the claims as attached.

What is claimed is:

1. An inspection method comprising:
   acquiring a radiation image of goods being inspected;
   processing on the radiation image to obtain an ROI;
   inspecting on the ROI using a liquor goods inspection model to determine if the ROI of the radiation image contains liquor goods, wherein the liquor goods inspection model is established based on a weighted sum of shape information and texture information of a feature in samples, and the weight is in association with a regional conditional entropy of the feature.

2. The inspection method according to claim 1, wherein the step of inspecting on the ROI using a liquor goods inspection model comprising:
   extracting shape information and texture information of a local target from the ROI;

classifying the shape information and the texture information of the local target from the ROI using the liquor goods inspection model established based on a weighted sum of shape information and texture information of a feature in the local target, so as to determine if the ROI of the radiation image contains liquor goods, the weight is in association with a regional conditional entropy of the feature.

3. The inspection method according to claim 1, wherein the ROI is inspected in multiple-scales using the liquor goods inspection model.

4. The inspection method according to claim 1, wherein the step of processing on the radiation image comprising:
   detecting on air regions and impenetrable regions in the radiation image;
   excluding the air regions and the impenetrable regions from the ROIs.

5. The inspection method according to claim 1, further comprising a step of:
   training the liquor goods inspection model by way of manually labeling using scanned images of known goods categories where liquor goods are contained and scanned images of goods that is similar to liquors but not liquors.

6. The inspection method according to claim 5, wherein the manually labeling comprises: labeling positions and placing postures of the liquor goods in the image.

7. The inspection method according to claim 5, wherein the liquor goods inspection model is established with respect to different placing postures of liquor goods.

8. The inspection method according to claim 1, further comprising a step of:
   for those liquor goods that are not detected using the liquor goods inspection model and those goods that are detected using the liquor goods inspection model as liquor goods but turns out to be non-liquor goods, re-training the liquor goods inspection model by manually labeling.

9. An inspection system comprising:
   a scanning imaging system configured to scan goods being inspected so as to acquire a radiation image of the goods being inspected;
   a data processing apparatus configured to process on the radiation image to obtain an ROI, and to inspect on the ROI using a liquor goods inspection model to determine if the ROI of the radiation image contains liquor goods, wherein the liquor goods inspection model is established based on a weighted sum of shape information and texture information of a feature in samples, the weight is in association with a regional conditional entropy of the feature.

10. The inspection system according to claim 9, wherein the data processing apparatus is configured to extract shape information and texture information of a local target from the ROI, and to classify the shape information and the texture information of the local target from the ROI using the liquor goods inspection model established based on a weighted sum of shape information and texture information of a feature in the local target so as to determine if the ROI of the radiation image contains liquor goods.

* * * * *